United States Patent
Hedges

(10) Patent No.: US 8,236,332 B2
(45) Date of Patent: Aug. 7, 2012

(54) PARTICLE STABILISED EMULSION COMPOSITION

(75) Inventor: Nicholas David Hedges, Sharnbrook (GB)

(73) Assignee: Conopco Inc., Englewood Cliffs, NJ (US)

( * ) Notice: Subject to any disclaimer, the term of this patent is extended or adjusted under 35 U.S.C. 154(b) by 363 days.

(21) Appl. No.: 12/284,538

(22) Filed: Sep. 23, 2008

(65) Prior Publication Data

US 2009/0087464 A1  Apr. 2, 2009

(30) Foreign Application Priority Data

Sep. 28, 2007 (EP) .................................. 07117503

(51) Int. Cl.
*A61K 8/06* (2006.01)
*A61Q 19/00* (2006.01)

(52) U.S. Cl. ...................................................... 424/401

(58) Field of Classification Search .................. None
See application file for complete search history.

(56) References Cited

U.S. PATENT DOCUMENTS

| | | | |
|---|---|---|---|
| 4,305,964 A | | 12/1981 | Moran et al. |
| 4,720,390 A | | 1/1988 | Bachler et al. |
| 4,966,892 A | * | 10/1990 | McAnalley ..................... 514/54 |
| 5,332,595 A | * | 7/1994 | Gaonkar ....................... 426/602 |
| 5,681,601 A | * | 10/1997 | Hendrick et al. .............. 426/99 |
| 6,136,363 A | * | 10/2000 | Bialek et al. ................. 426/573 |
| 6,831,107 B2 | * | 12/2004 | Dederen et al. .............. 514/777 |
| 2001/0041207 A1 | * | 11/2001 | Brown et al. ................ 426/573 |
| 2006/0110517 A1 | | 5/2006 | Carle et al. |
| 2006/0222670 A1 | | 10/2006 | Armes et al. |
| 2008/0305056 A1 | * | 12/2008 | Jenni et al. ..................... 424/59 |

OTHER PUBLICATIONS

XP-002471609 & JP 59 139310 A (Shiseido Co. Ltd.) Aug. 10, 1984—Abstract.

* cited by examiner

*Primary Examiner* — Robert A Wax
*Assistant Examiner* — Danah Al-Awadi
(74) *Attorney, Agent, or Firm* — Karen E. Klumas

(57) ABSTRACT

The present invention relates to emulsifier system comprising food-grade gelled particles and the preparation of particle stabilised emulsions with this emulsifier. The emulsifier system can be used in any fields of applications, such as food products, home and personal care applications and pharmaceutical applications.

13 Claims, 25 Drawing Sheets

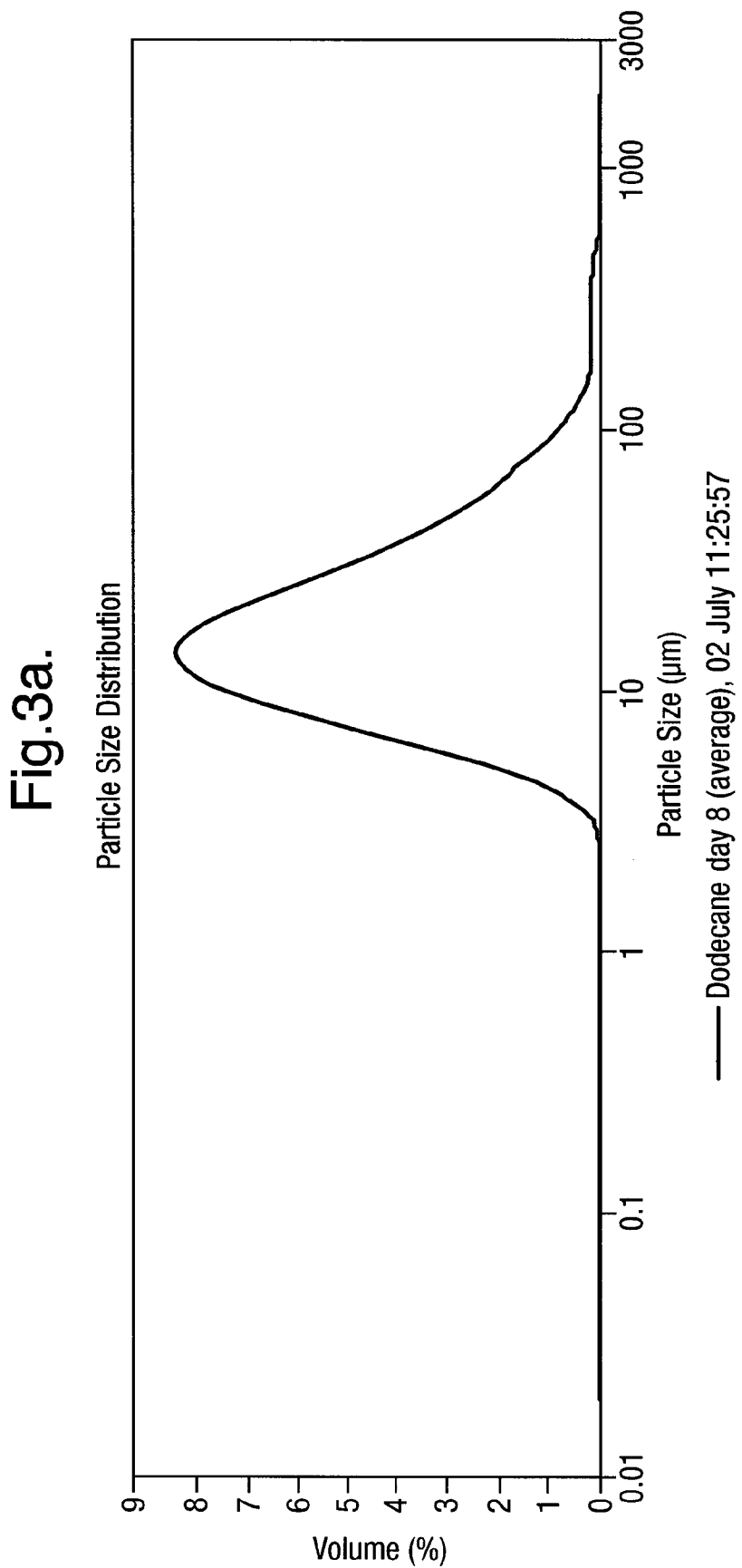

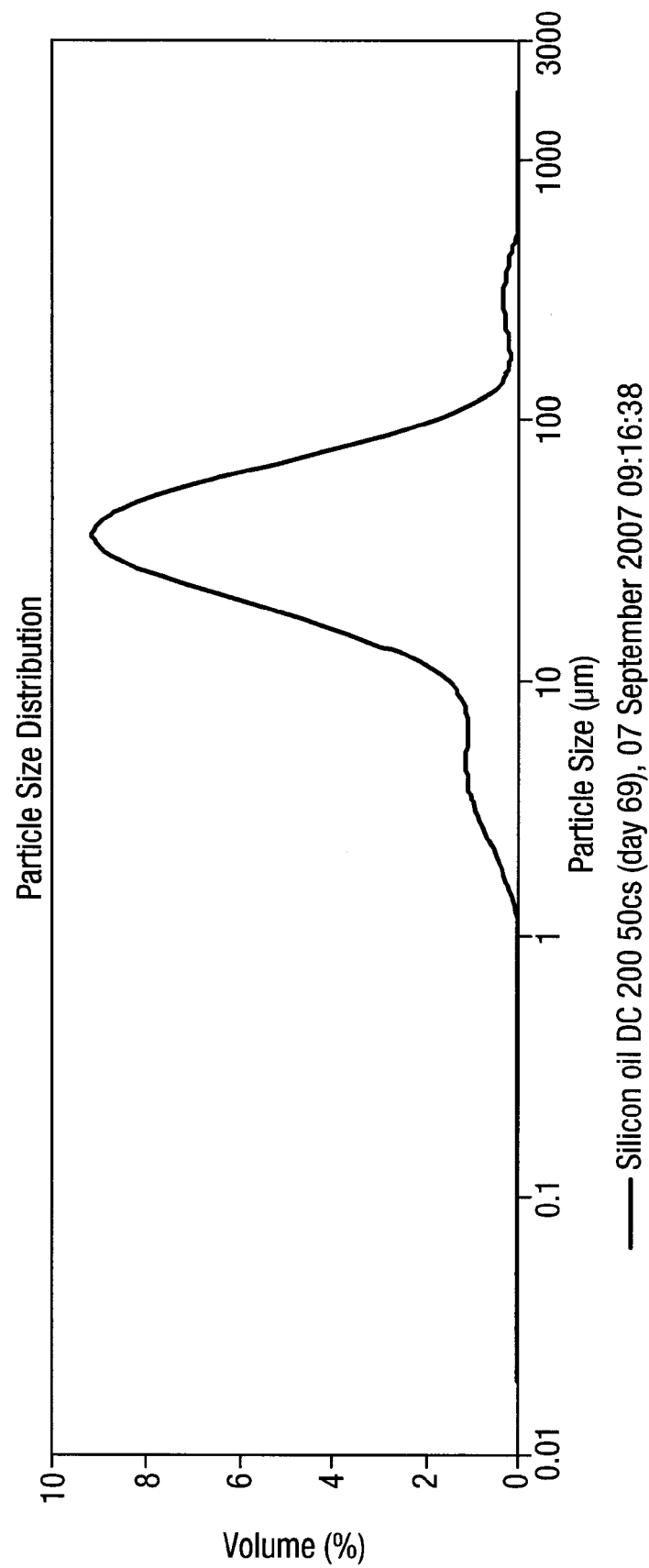

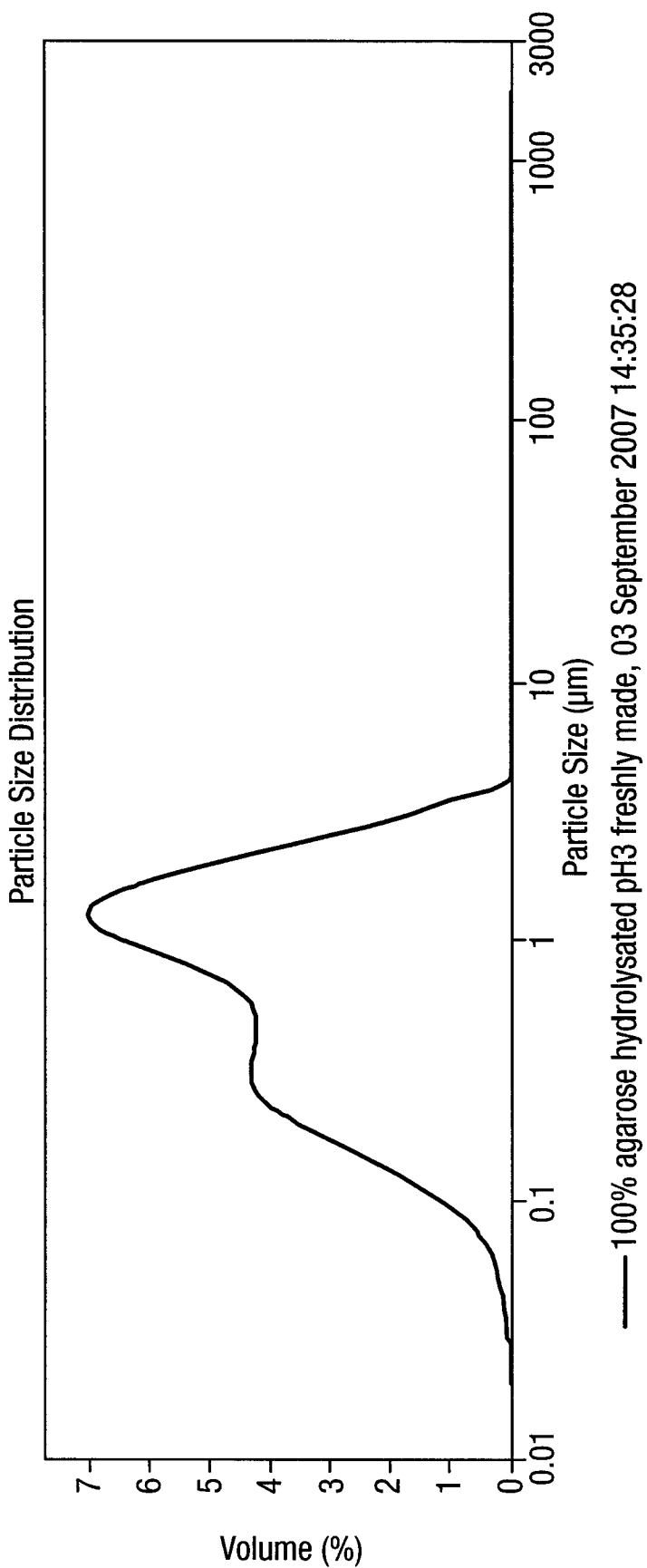

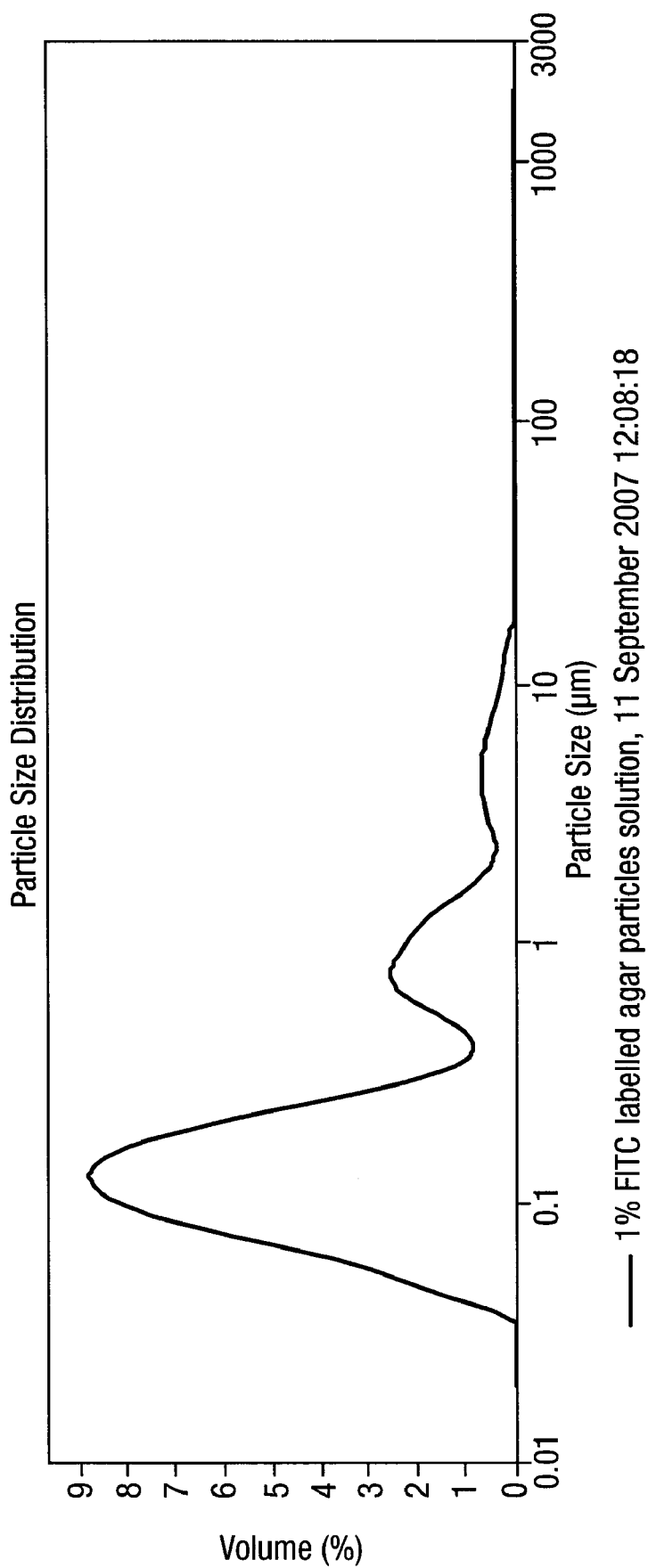

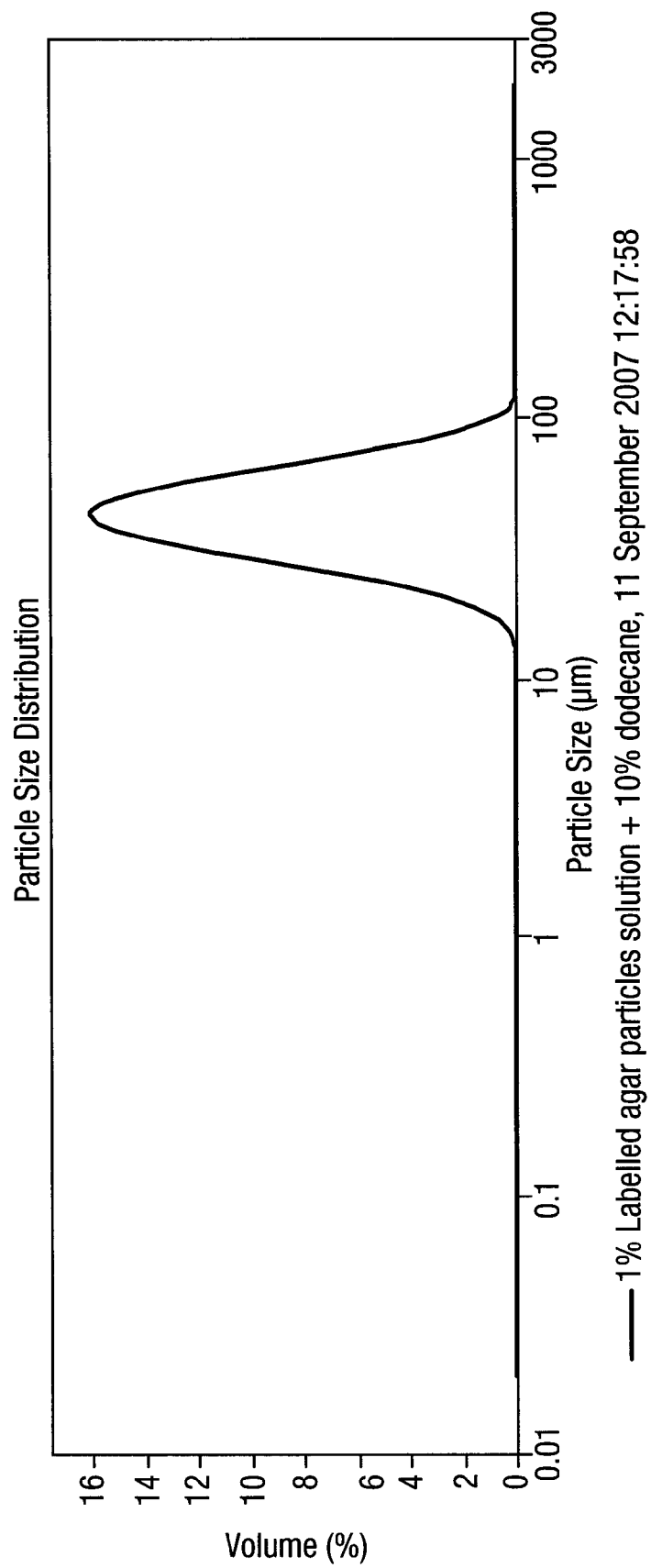

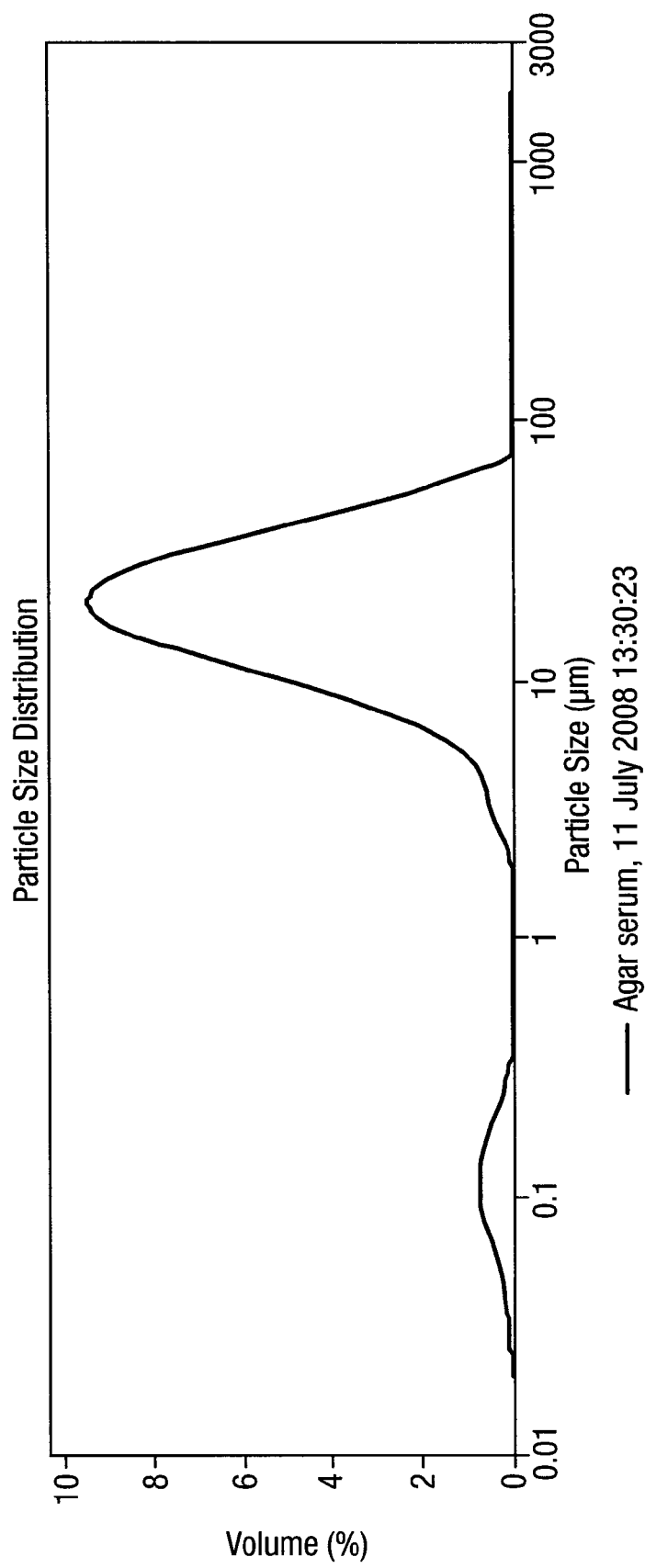

PARTICLE STABILISED EMULSION COMPOSITION

The present invention relates to an emulsion composition comprising gelled particles derived from naturally occurring food-grade polymers, the emulsion composition being selected from the group consisting of food products, home care products, personal care products and pharmaceutical products.

Emulsifiers are limited in their use as they can cause allergic reactions in some people. There is thus a constant need for alternative emulsifiers. The goal of the present invention is to provide a stable emulsion composition which can be used in a wide number of applications.

The term "food-grade" means compounds, which are safe for use in food as defined by governmental institutes such as the FDA in the US or the WHO. In Europe food grade may be defined as an ingredient that has an E number. For example, agar is E406, gellan is E418 and pectins are E440.

SUMMARY OF THE INVENTION

Thus the invention provides an emulsion composition comprising as an emulsifier 0.5-25.0% by weight of the composition of gelled particles, wherein the gelled particles have a largest dimension of 3-1000 nm, preferably 5-500 nm and most preferably 10-200 nm, wherein the gelled particles comprise at least one gellable polysaccharide.

By the term "largest dimension" is meant the longest straight dimension that can be measured on the particle. The largest dimension of the gellable particles can be determined by any commonly known processes such as electron microscopy or light scattering methods. Typically the ratio of the largest dimension of the droplets which form the dispersed phase of the emulsion composition to the largest dimension of the gelled particles is in the range 10:1-10000:1, preferably 10:1-1000:1. It has been observed that the superior emulsion stability provided by the gellable particles of the invention allows stabilisation of larger droplets up to a largest dimension of about 100 microns.

The gelled particles have, when in use, a water content of 30-99.95%, typically 90-95% by weight based on the total weight of the gelled particles. Thus the gelled particles are softer and less abrasive and therefore the inventive emulsion compositions may be used in applications where harder abrasive particles would not be preferred.

It has been noted that polysaccharides, most of which are naturally occurring food-grade polymers, are normally used to form open and extensive gel networks for use as, for example, thickeners and gelling agents, rather than gelled particles. Thus the polysaccharides must undergo processing in order to form gelled particles as detailed hereinbelow.

Preferably the emulsion composition comprises as an emulsifier 0.5-10.0%, more preferably 0.5-5.0% by weight of the composition of gelled particles.

The gelled particles can have an aspect ratio in the range of 1:1 to 10:1. Preferably the gelled particles are in the form of spheres, disks or rods.

The gellable polysaccharide may be selected from the group consisting of agar, agarose, gellan and pectin. Preferred gellable polysaccharides are neutral or weakly charged polymers such as agar or agarose although charged polymers may be used depending on the pH and ionic strength.

Preferably the emulsion composition comprises no further emulsifier.

The gelled particles can be formed by any method that provides particles of the correct size and surface properties. The method will typically begin with forming a solution of polymer followed by one or more process steps including chemical treatment or enzymatic treatment of the polymer and cooling, mixing, drying, freezing and concentrating. In one method a hot solution of polymer is prepared and the polymer chains hydrolysed such that on cooling a suspension of particles rather than a gel forms. Hydrolysis may be carried out using any suitable method such as acid or enzymatic hydrolysis.

The emulsion composition may be selected from the group consisting of food products, home care products, personal care products and pharmaceutical products. The emulsion is in the form of an oil-in-water emulsion, a water-in-oil emulsion or multiple emulsions such as oil-in-water-in-oil emulsions or water-in-oil-in water emulsions. A preferred form is as an oil-in-water emulsion or as a multiple emulsion. It has been observed that particle stabilised emulsions are very stable. In particular the particles do not appear to migrate from the oil-water interface and thus are particularly useful when employed to stabilise multiple emulsions where there are a plurality of oil-water interfaces.

SUMMARY OF THE FIGURES

The invention is now illustrated with reference to the following figures which show in:

FIG. 6 the particle size distribution for the agarose gelled particles of example 4 in the absence of sonication obtained by light scattering.

FIG. 8 the particle size distribution for the fluorescently labelled agarose gelled particles of example 5 in the absence of sonication obtained by light scattering;

FIG. 9 the oil droplet size distribution of a dodecane-in-water emulsion stabilised by the fluorescently labelled agar gelled particles of example 5 obtained by light scattering;

DETAILED DESCRIPTION OF THE INVENTION

EXAMPLE 1

Preparation of Agar Gelled Particles

Deionised water was heated to above 95° C., 1% by weight agar powder (Luxara agar (code:1253) from Arthur Branwell Ltd) Added and the mixture heated until all the agar had dissolved. The resulting solution was cooled to 70° C., the pH adjusted to 3.0 with citric acid and the solution held at 70° C. for 150 minutes under stirring. The pH was then reduced to 1.0 with dilute HCl and held at 70° C. for a further 15 minutes. Finally the mixture was then cooled to chill temperature (around 5° C.)) and stored until required.

The hydrolysate was allowed to sediment overnight and supernatant decanted. The lower layer was shaken to mix well and transferred to 50 ml centrifuge tubes. The hydrolysate was separated by centrifugation for 10 minutes at 3000 rpm on a MSE Centaur 2 bench centrifuge and the supernatant decanted. The resulting pellet of hydrolysate was resuspended in approximately five times its volume of deionised water and centrifuged once more and the process repeated twice more. The hydrolysate was stored at chill temperature in a 0.025M solution of citric acid until used.

Figure 1:
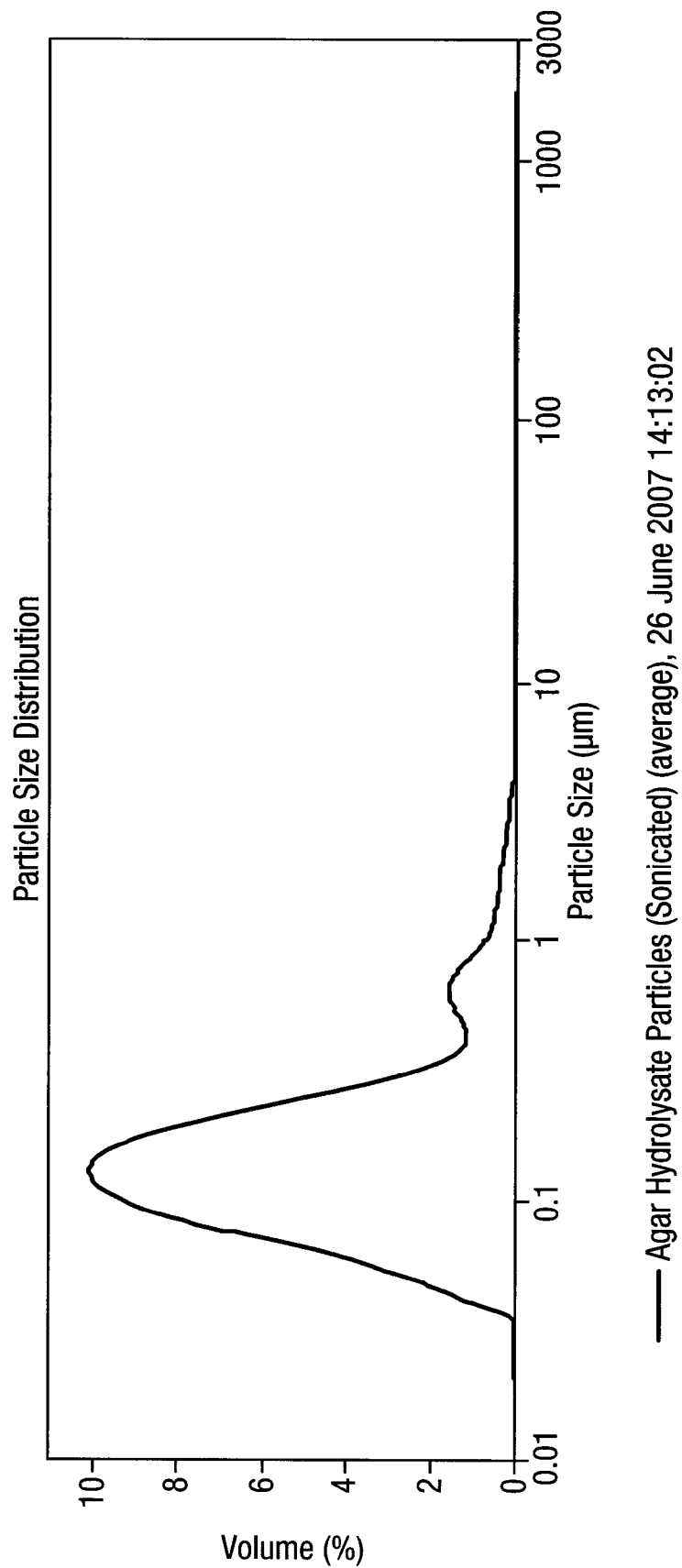
FIG. 1 the particle size distribution of the agar gelled particles of example 1 obtained by light scattereing.
Figure 2:
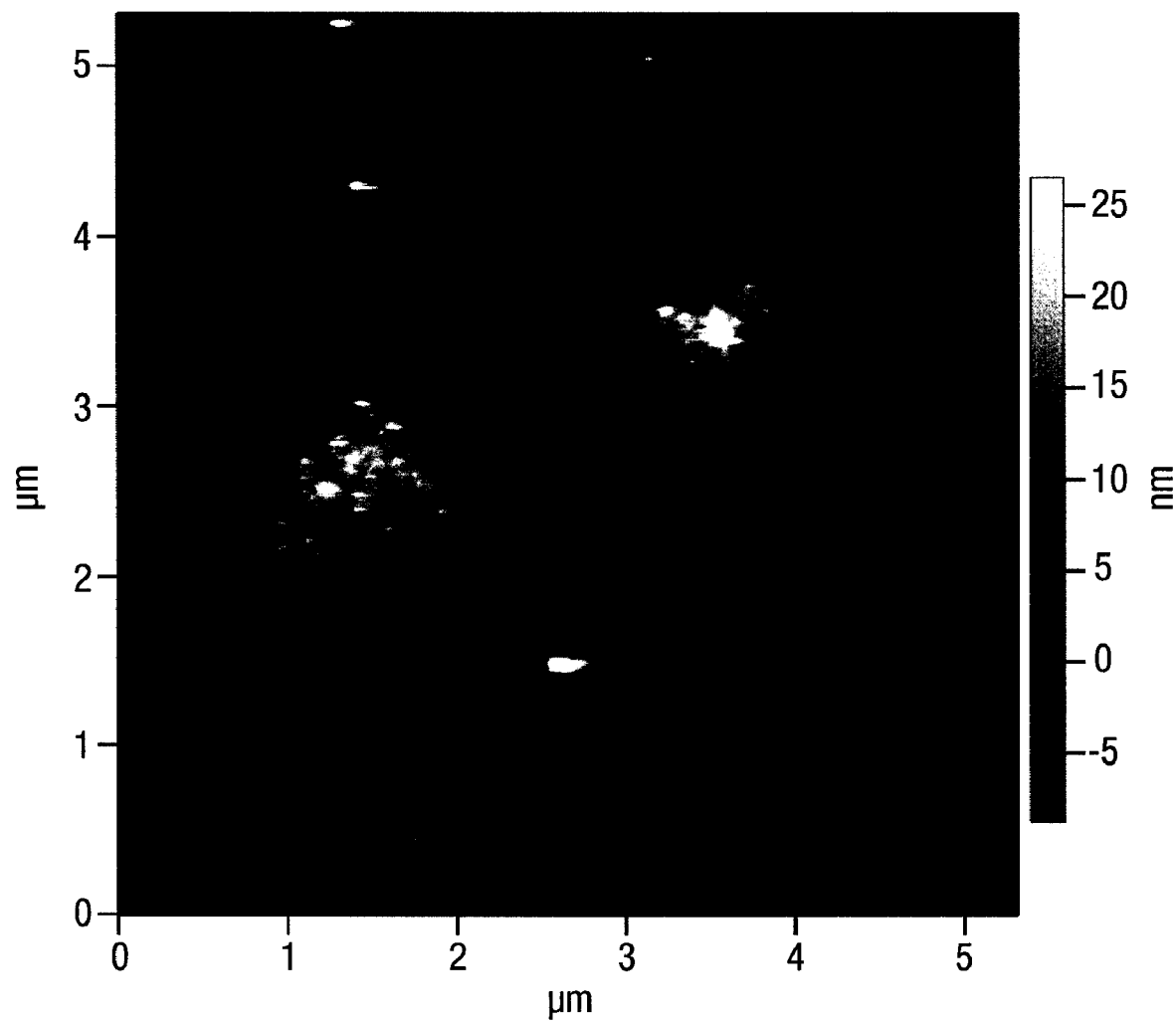
FIG. 2 an AFM image of the unsonicated agar gelled particles of example 1.

The particle size was determined using the Malvern Mastersizer 2000 fitted with the small volume sample dispersion unit in deionised water at room temperature. The refractive indices of the dispersing medium and the dispersed particles were 1.33 and 1.335 respectively and the analysis model was the General Purpose Spherical Model. The sample was sonicated in a bath for 1 minute prior to measurement and the results shown in FIG. 1. The result indicates that the particle size lies in the range 33-1000 nm. An atomic force microscopy (AFM) image was obtained on an MFP-3D-IO instrument (Asylum Research, California) by placing a drop of 0.1% w/w agar gelled particle dispersion onto a mica substrate and leaving it to adsorb over a period of 5 minutes. The sample was then rinsed to remove excess material not bound to the surface and dried. FIG. 2 shows an AFM image of unsonicated agar gelled particles indicating that aggregates are of the order of 1000 nm in diameter and have a thickness of about 25 nm.

EXAMPLE 2

Figure 3B:
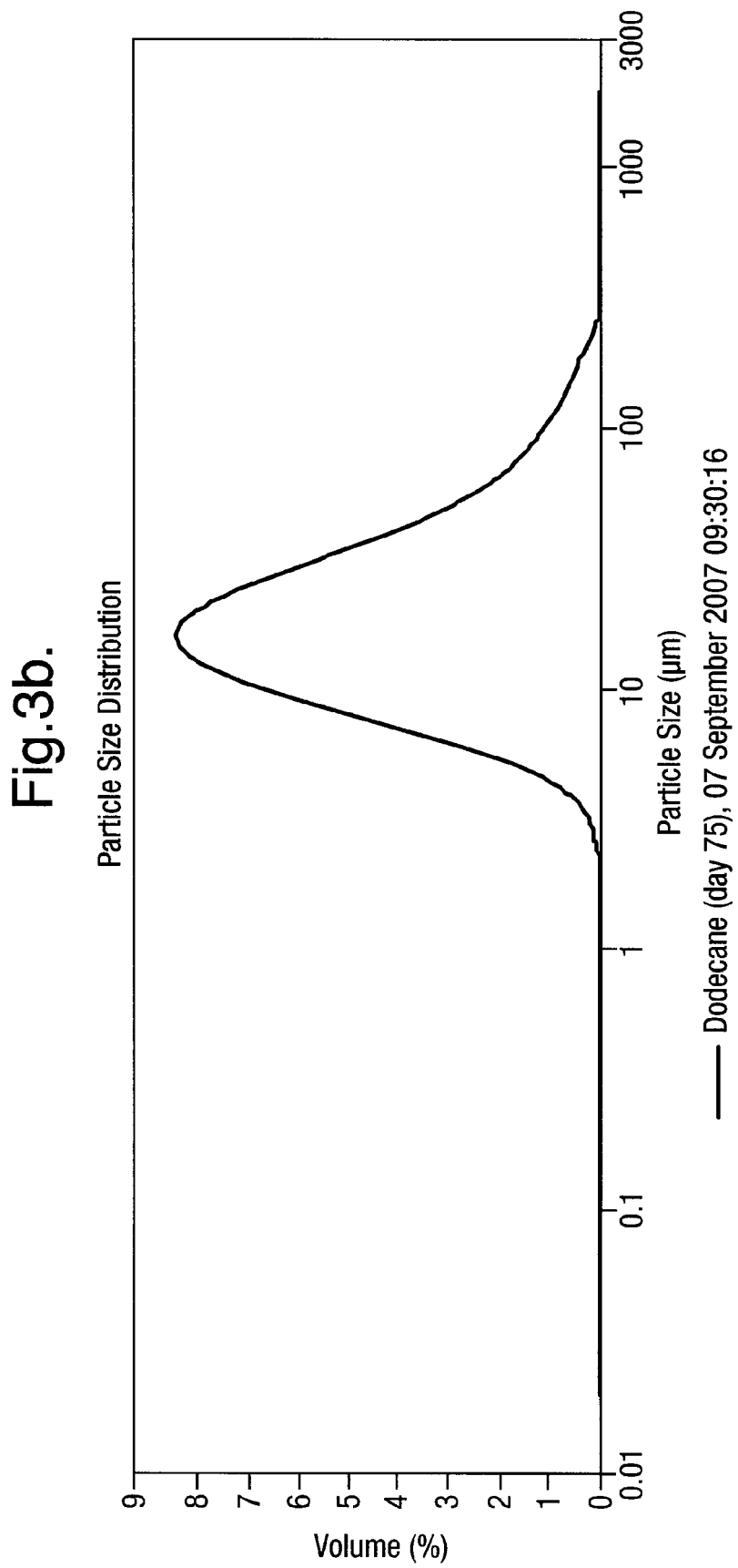
FIG. 3 the oil droplet size distribution of a dodecane-in-water emulsion composition stabilised by agar gelled particles according to example 2 obtained by light scattering after storage at 4 degrees centigrade for 8 (FIG. 3a) and 75 days (FIG. 3b) respectively.
Figure 4:
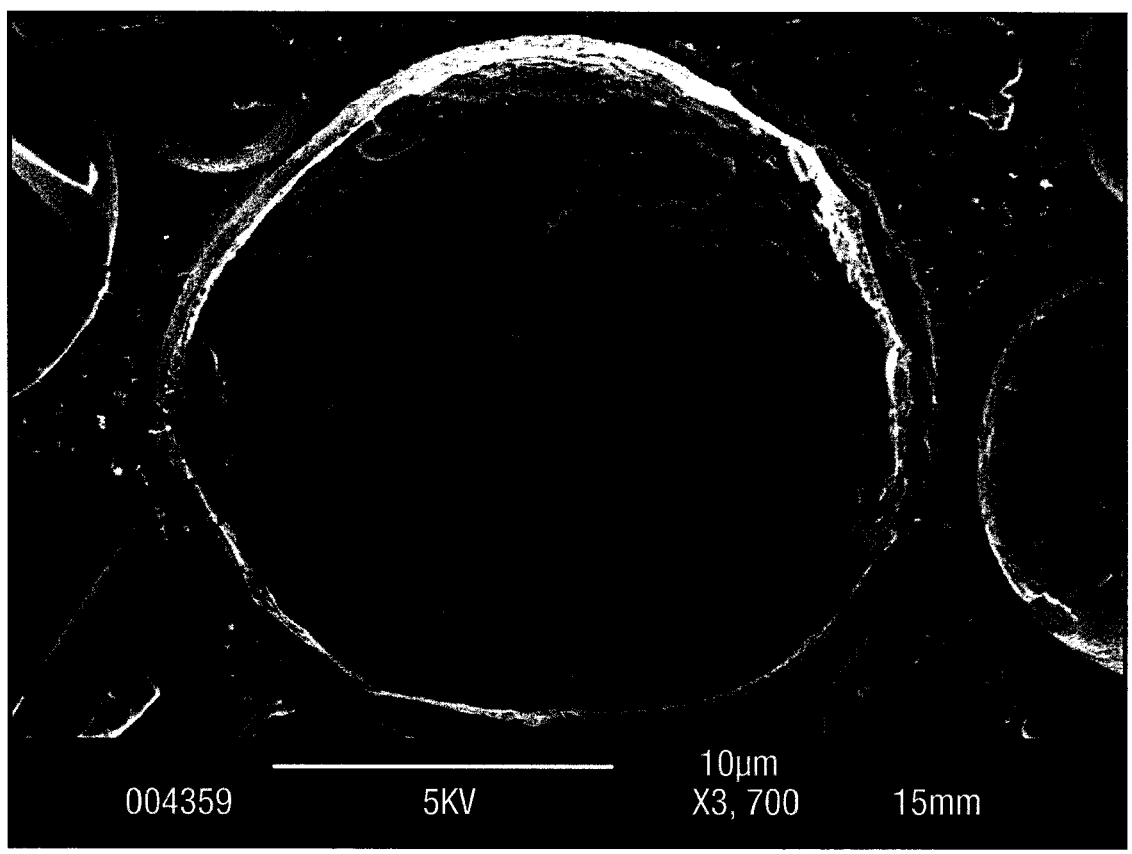
FIG. 4 a cryo-SEM image of a dodecane oil droplet from the emulsion of example 2 of about 20 µm in diameter surrounded by a 20 nm layer of agar gelled particles.

Preparation of a Dodecane-in-Water Emulsion Composition Stabilised by Agar Gelled Particles 1 gram of the agar gelled particles of example 1 was resuspended in 99 grams of 0.1% citric acid solution and 90 g of this suspension mixed with log of dodecane and subjected to emulsification using a Silverson L4R mixer. The pH of the emulsion was 3.0. FIGS. 3a and 3b show the oil droplet size distribution of the emulsion obtained using the Malvern Mastersizer 2000 with the method outlined in example 1 (the refractive index of the dodecane droplets was set to 1.421) after storage at 4 degrees centigrade for 8 and 75 days respectively indicating good emulsion stability. The size of the oil droplets produced was about 10-20 μm. A cryogenic Scanning Electron Microscopy (cryo-SEM) image was taken on a JEOL 63/OF field emission scanning electron microscope by rapidly freezing a sample using a liquid nitrogen slush followed by evaporation of the water. FIG. 4 shows a cryo-SEM image of a dodecane oil droplet of about 20 μm in diameter surrounded by a 20 nm layer of agar gelled particles.

EXAMPLE 3

Figure 5A:
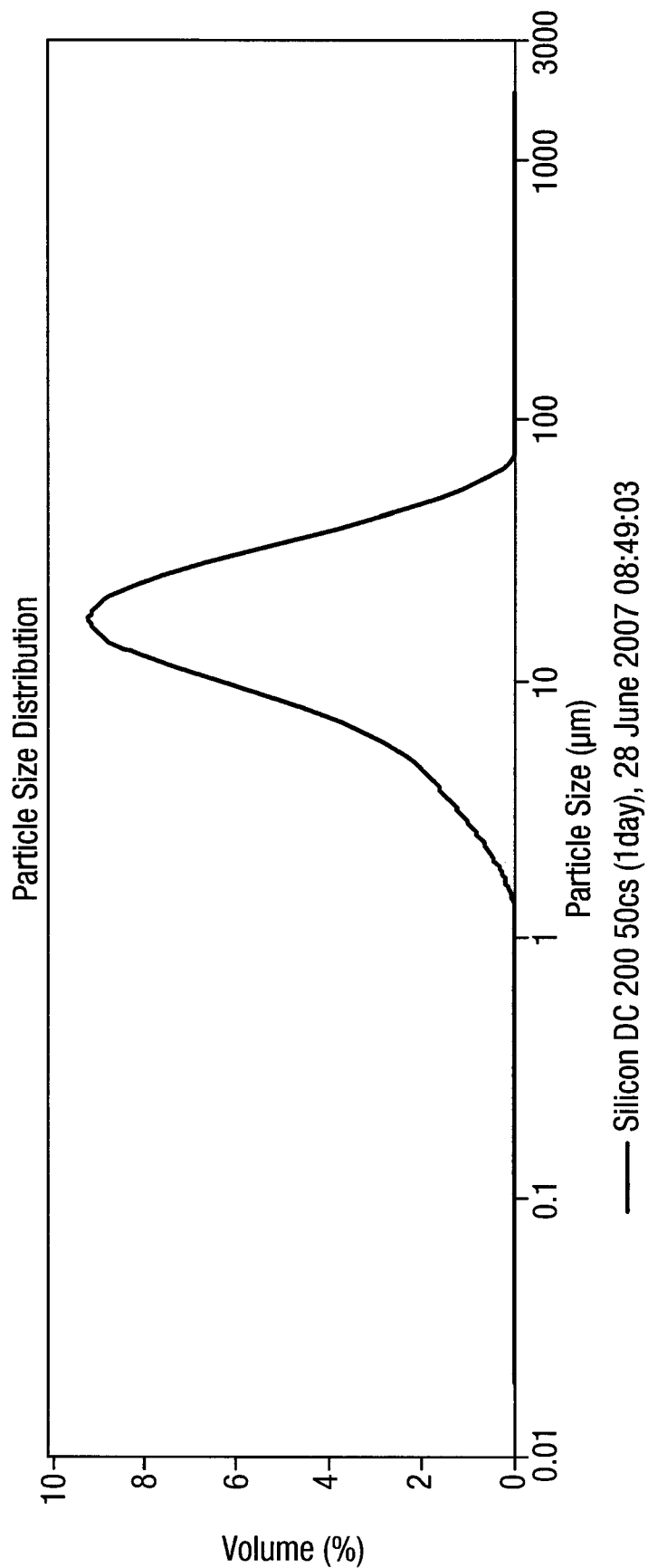
FIG. 5 the oil droplet size distribution of the emulsion obtained by light scattering with the method outlined in example 1 after storage at 4 degrees centigrade for 1 (FIG. 5a) and 69 (FIG. 5b) days respectively.

Preparation of a Silicon Oil-in-Water Emulsion Stabilised by Agar Gelled Particles A silicon oil-in-water emulsion stabilised by agar gelled particles was prepared in the same way as for example 2 except that the dodecane was substituted by DC200-50 cs silicon oil from Dow Coming. The pH of the emulsion was 3.0. FIGS. 5a and 5b show the oil droplet size distribution of the emulsion obtained using the Malvern Mastersizer 2000 with the method outlined in example 1 (the refractive index of the silicon oil droplets was set to 1.403) after storage at 4 degrees centigrade for 1 and 69 days respectively indicating good emulsion stability.

EXAMPLE 4

Figure 7A:
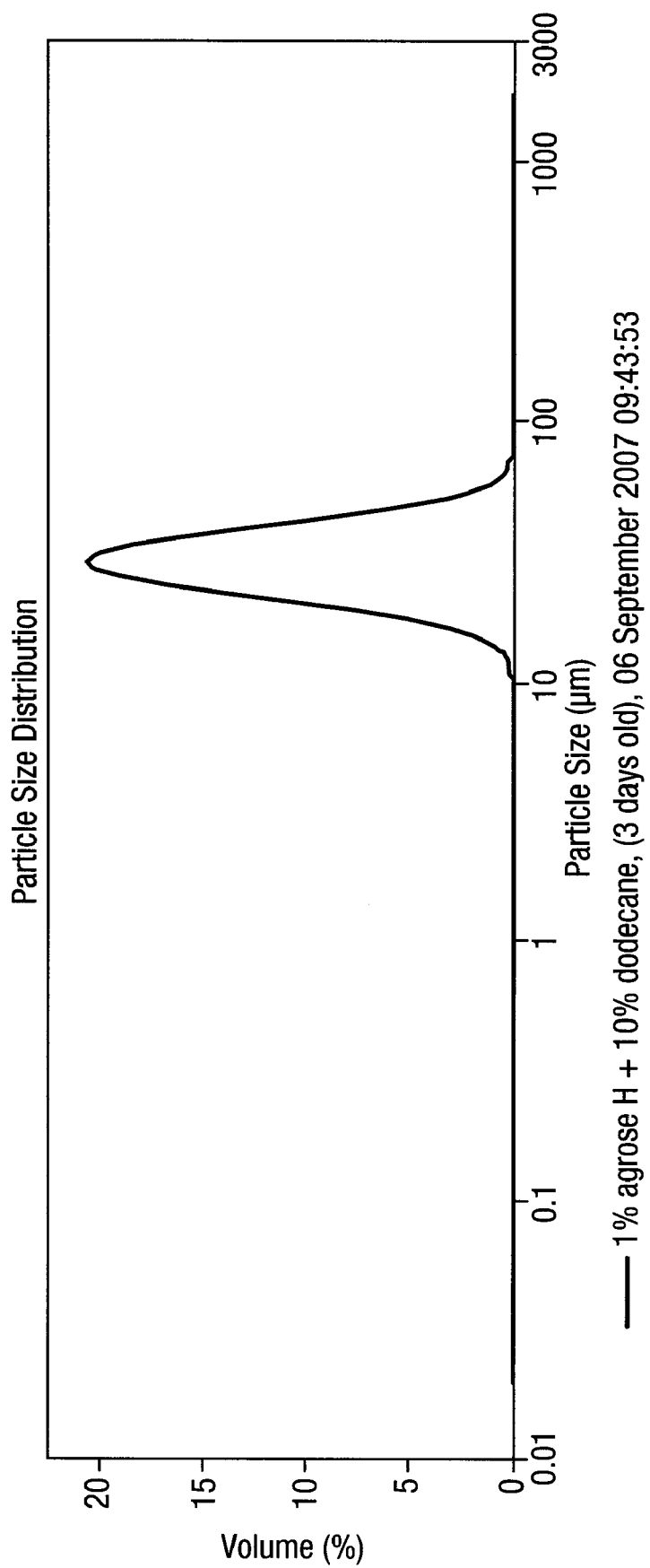
FIG. 7 the oil droplet size distribution of the dodecane-in-water emulsion stabilised by agarose gelled particles of example 4 obtained by light scattering after storage at 4 degrees centigrade for 3 (FIG. 7a) and 25 (FIG. 7b) days respectively.
Figure 7B:
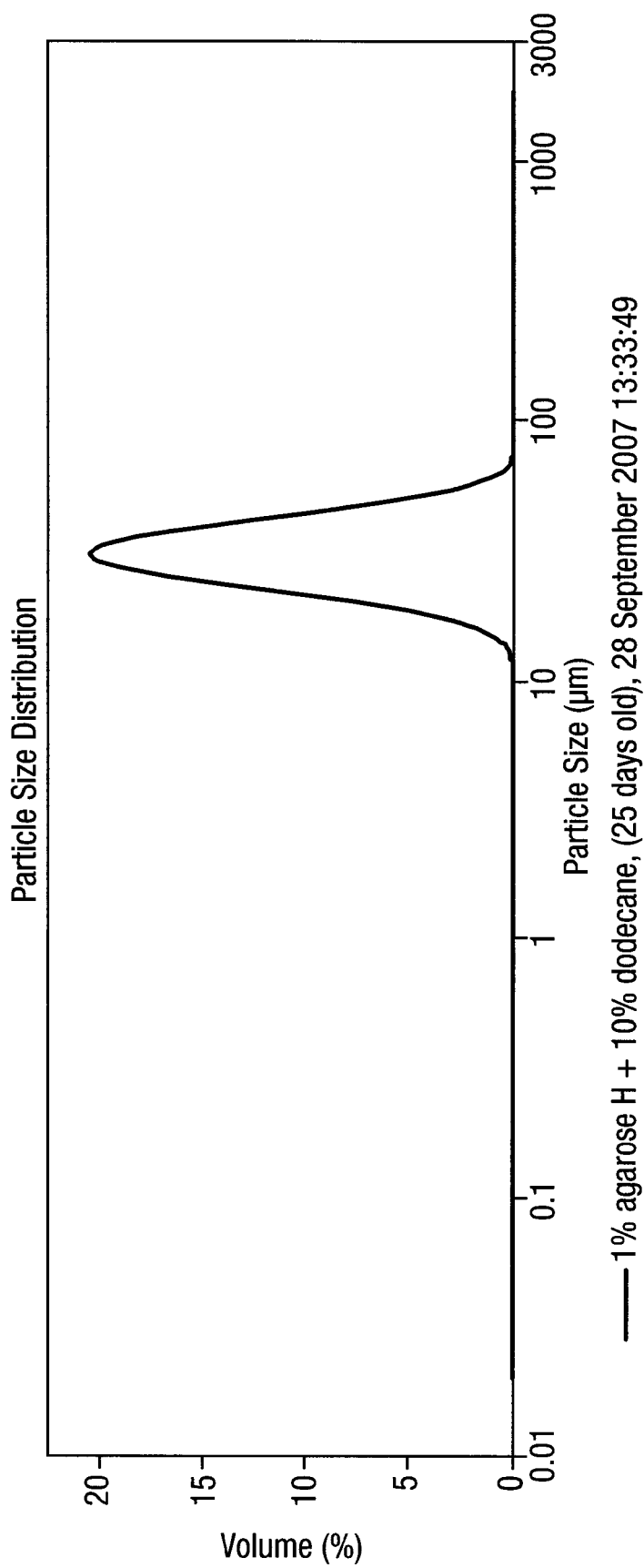

Preparation of a Dodecane-in-Water Emulsion Stabilised by Agarose Gelled Particles Agarose gelled particles were prepared by adapting the method of example 1 by substituting agar with Sigma type I low EEO agarose. FIG. 6 shows the particle size distribution for the agarose gelled particles in the absence of sonication as measured by the method described in example 1. The result indicates that the particle size lies in the range 33-1000 nm. A dodecane-in-water emulsion stabilised by agarose gelled particles was prepared in the same way as for example 2 except that the agar gelled particles were substituted by the agarose gelled particles. The pH of the emulsion was 3.0. FIGS. 7a and 7b show the oil droplet size distribution of the emulsion obtained using the Malvern Mastersizer 2000 with the method outlined in example 1 after storage at 4 degrees centigrade for 3 and 25 days respectively indicating good emulsion stability.

EXAMPLE 5

Preparation of a Dodecane-in-Water Emulsion Stabilised by Fluorescently Labelled Agar Gelled Particles 1 g of Agar (Luxara Agar (code 1253) from Arthur Branwell Ltd) was dissolved in 10 ml dimethyl sulphoxide (DMSO) containing 2 drops of pyridine. 0.10 g of 90% fluorescein isothiocyanate (FITC) from Aldrich was added along with 1 drop of the Tin(II) 2-ethyl hexanoate (Sigma Aldrich, 95% pure). The solution was placed in a hot oil bath at 95° C. for 2 hours under stirring. 50 cm$^3$ of ethanol was then added to the hot solution and a product precipitated out of solution. The precipitate was collected by vacuum filtration and washed with 50cm$^3$ of ethanol and the washing procedure repeated until the ethanol filtrate was dear. This process removed excess unreacted FITC. The precipitate was then dried in a vacuum oven at 80° C. overnight and dissolved in hot ethylenediamine tetraacetic acid solution (90° C., 0.2%) and stirred at 90° C. for 2 hours. The solution was then transferred into dialysis tubing with an 8000 molecular weight cut off and placed in a dialysis bath of deionised water. Dialysis was carried out for 2 days with at least 5 changes of water. The solution was removed from the dialysis tubing and freeze dried. FIG. 8 shows the particle size distribution for the agarose gelled particles in the absence of sonication as measured by the method described in example 1. The result indicates that the particle size lies in the range 33-1000 nm.

Figure 10A:
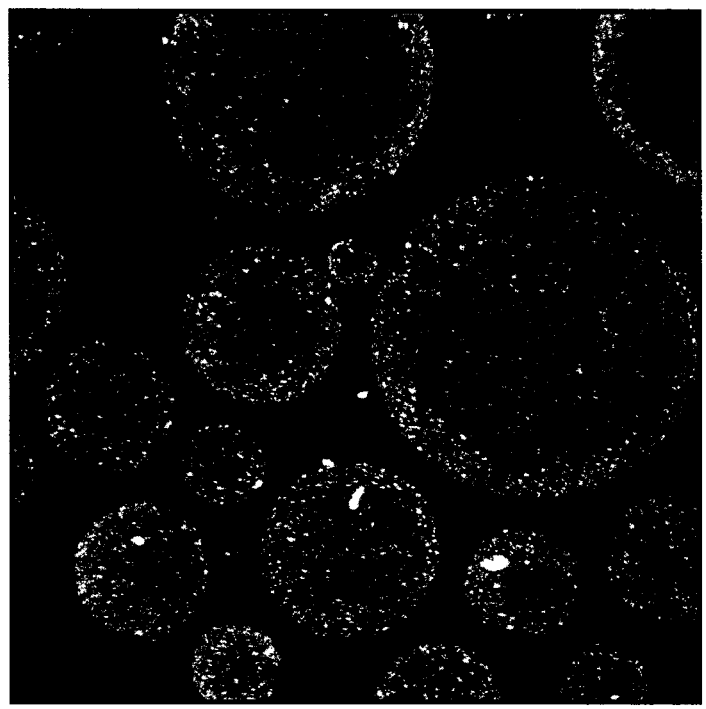
FIG. 10 confocal fluorescence images of fluorescently labelled agar gelled particles covering the dodecane oil droplets (FIG. 10a) and surrounding a section through the dodecane droplets (FIG. 10b) of the emulsion of example 5 (image width of 160 microns)
Figure 10B:

A dodecane-in-water emulsion was prepared stabilised by the fluorescently labelled agar gelled particles using the method described in example 2. The pH of the emulsion was 3.0. FIG. 9 shows the oil droplet size distribution of the emulsion obtained using the Malvern Mastersizer 2000 with the method outlined in example 1. Confocal fluorescence images of the emulsion were obtained on a Leica TCS SP Confocal Scanning Laser Microscope at a wavelength of 488 nm. FIGS. 10a and 10b show the fluorescently labelled agar gelled particles covering the dodecane oil droplets (FIG. 10a) and surrounding a section through the dodecane droplets (FIG. 10b).

EXAMPLE 6

Preparation of a Skin Serum Formulation Using Agar Gelled Particles

The following skin care serums were prepared. The formulations were practically identical save that the control formulation included Polysorbate 20 and the test formulation included the agar gelled particles of example 1 as emulsifiers.

| Material Trade Name | Control (% w/w) | Test (% w/w) |
| --- | --- | --- |
| Water | 51.55 | 49.45 |
| Glycerine | 17.00 | 17.00 |
| Dicaprylyl ether | 10.00 | 10.00 |
| Polydimethlysiloxane | 10.00 | 10.00 |
| Caprylic/caprylic acid triglyceride | 10.00 | 10.00 |
| Carbopol 5984 in Synthalen M | 0.25 | 0.25 |
| Triethanolamine | 0.20 | 0.20 |
| Agar particles | 0.00 | 3.00 |
| Polysorbate 20 | 1.00 | 0.00 |
| Sodium chloride | 0.00 | 0.10 |

Figure 11A:
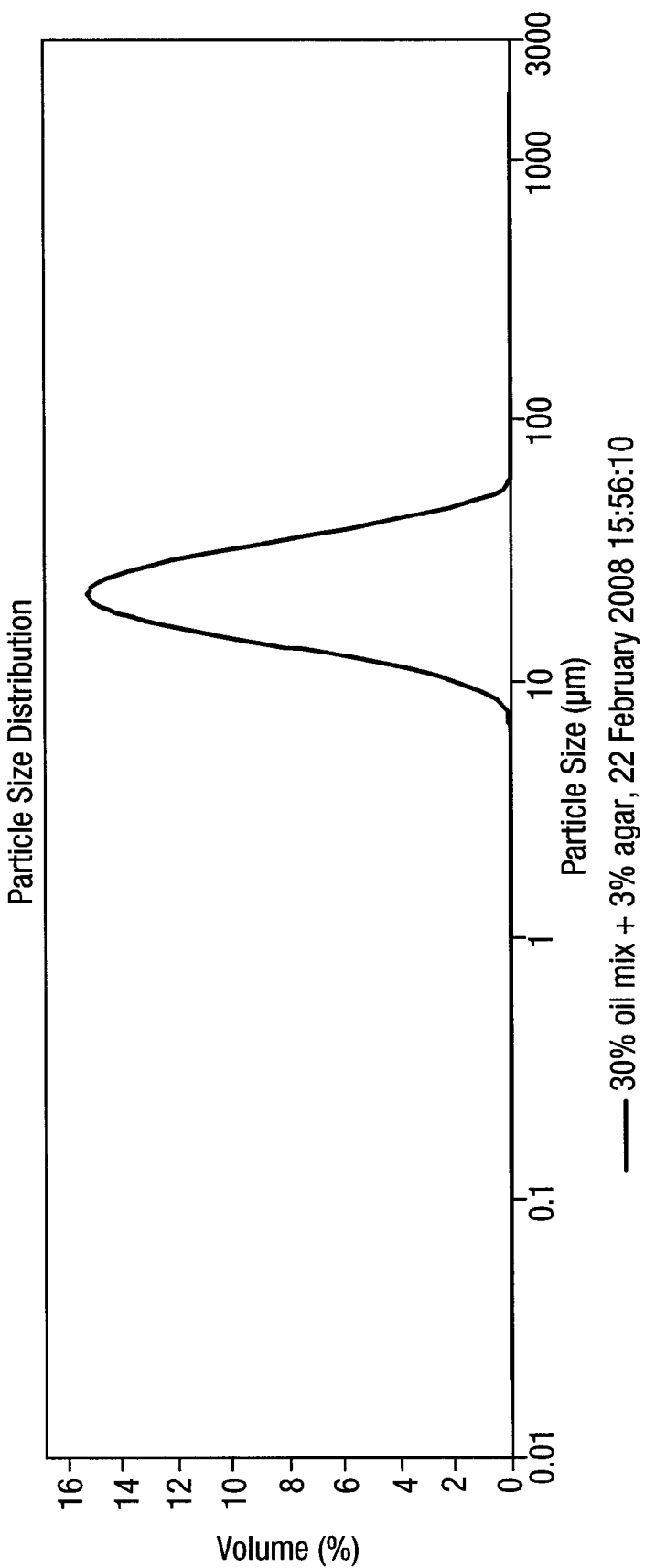
FIG. 11 the oil droplet size distribution of the test emulsion of example 6 obtained by light scattering after storage at 4 degrees centigrade for 0 (FIG. 11a) and 170 (FIG. 11b) days respectively indicating good emulsion stability.

The test formulation was prepared by dispersing the Carbopol 5894, agar particles and sodium chloride in water. Separately the polydimethlysiloxane, caprylic/caprylic acid triglyceride and dicaprylyl ether were mixed together and then added to the aqueous phase and emulsified using a Silverson L4R high shear mixer at full power for 5 minutes. After emulsification the triethanolamine was immediately added to neutralise the Carbopol 5894 and therefore to thicken the emulsion before the glycerol was added and the emulsion mixed for a further 30 seconds at high speed. The control formulation was prepared as for the test formulation except that agar particles and sodium chloride were replaced by Polysorbate 20 and the mixture emulsified at high speed for 1 minute instead of 5 minutes in order to keep the oil droplet sizes of the two emulsions approximately the same. FIGS. 11a and 11b show the oil droplet size distribution of the test emulsion obtained using the Malvern Mastersizer 2000 with the method outlined in example 1 (the refractive index of the oil droplets was set to 1.421) after storage at 4 degrees centigrade for 0 and 170 days respectively indicating good emulsion stability.

Figure 12A:
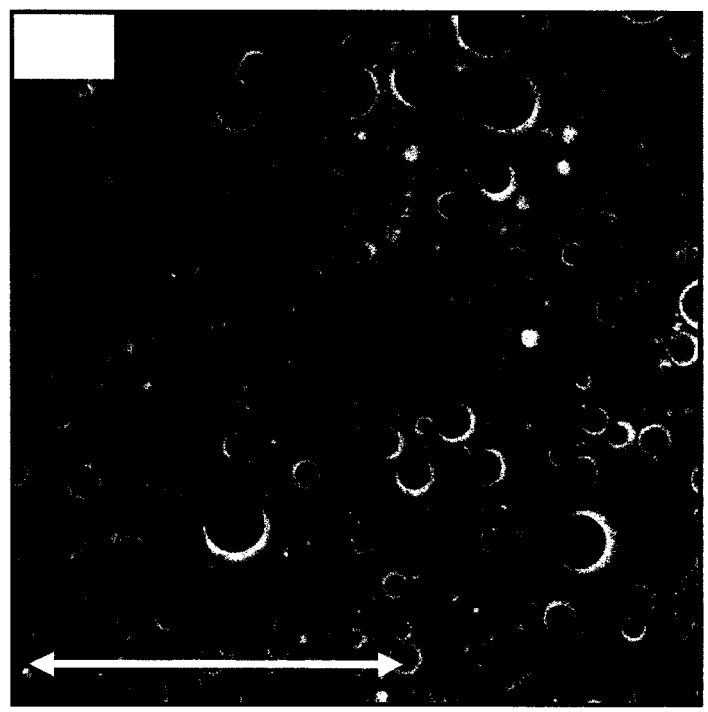
FIG. 12 confocal fluorescence images of the control (FIG. 12a) and test (FIG. 12b) emulsions of example 6 respectively (bar is 500 microns)
Figure 12B:
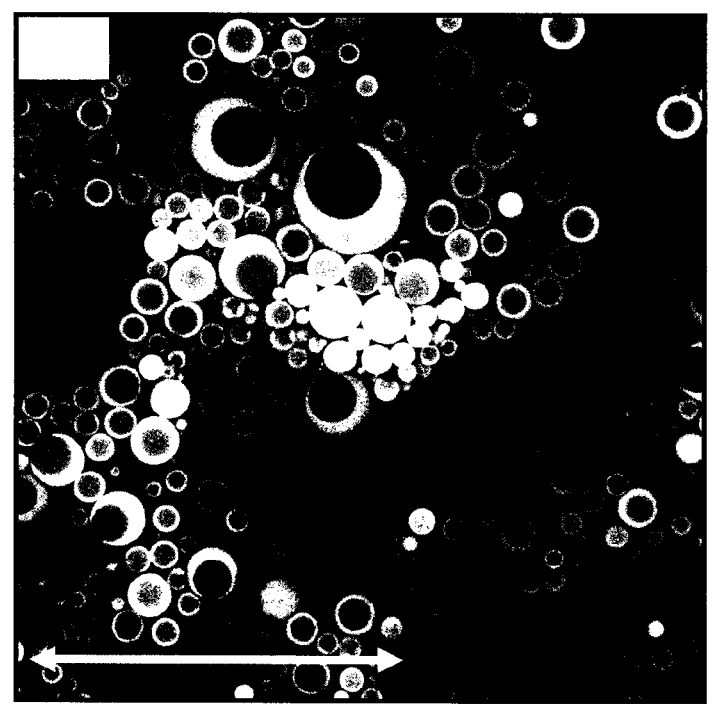
Figure 13A:
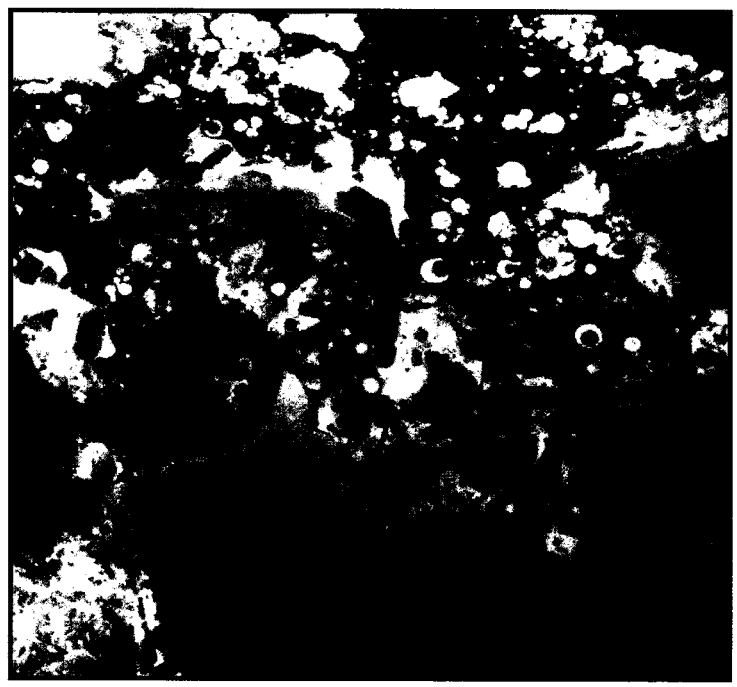
FIG. 13 confocal fluorescence images of the control (FIG. 13a) and test (FIG. 13b) emulsions of example 6 respectively applied to pig skin after vigorous rubbing (same magnification as for FIG. 12)
Figure 13B:
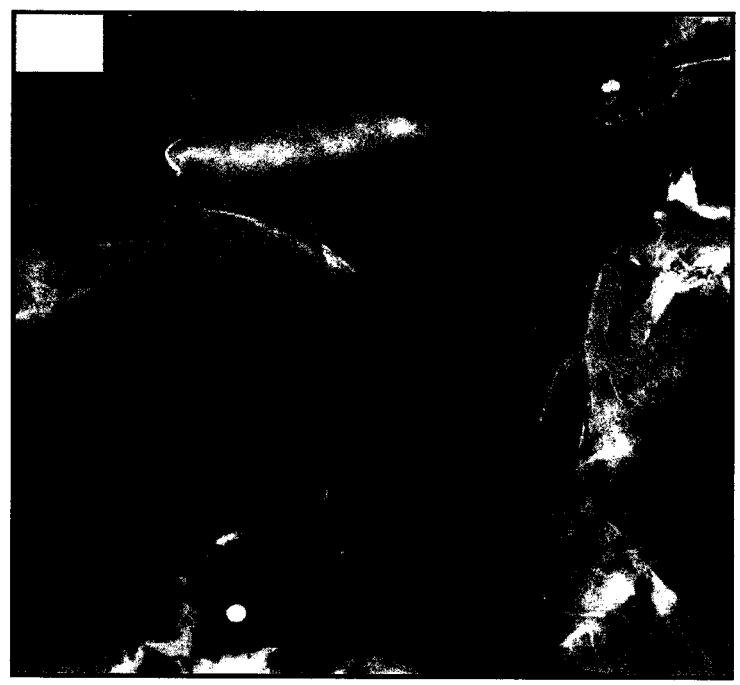

FIGS. 12a and 12b show confocal fluorescence images of the control and test emulsions respectively obtained on a Leica TCS SP Confocal Scanning Laser Microscope at a wavelength of 488 nm. The emulsions were each mixed with a fluorescence marker (Nile Blue Sulphate from Sigma) in a ratio of 9 parts by weight emulsion and 1 part by weight 0.1% w/w Nile Blue Sulphate in distilled water. Although Nile Blue Sulphate is water soluble, it is more soluble in oil and preferentially partitions into the oil phase. FIGS. 13a and 13b show confocal fluorescence images of the control and test emulsions respectively applied to pig skin after vigorous rubbing by applying approximately 100 microlitres of each emulsion to approximately 1 cm$^2$ of pig skin and then rubbing it with a spatula. It is apparent that the structure of the control emulsion changes little whereas that of the test emulsion appears to have broken down releasing and spreading the oils onto the pig skin surface thereby enabling better delivery of the oils and any oil soluble actives present in the emulsion onto the skin.

EXAMPLE 7

Preparation of a Dodecane-in-Water-Emulsion Stabilised with Gellan Gelled Particles Over 2 hours 1% w/w of gellan powder (Kelcogel F Gellan from CP Kelco) was stirred into water at 100° C. and the pH lowered to 3.0 with citric acid during which the gellan was hydrolysed process to yield a viscous solution (rather than a gel). The solution was then allowed to cool to room temperature and any particulate matter collected by centrifugation for 10 minutes at 2500 rpm on a MSE Centaur 2 centrifuge. The particulate matter was resuspended in approximately 5 times their volume of deionised water and centrifuged once more and the process repeated twice more. The particulate matter was then stored at chill temperature (4° C) in 0.025M solution of citric acid until required.

Figure 14:
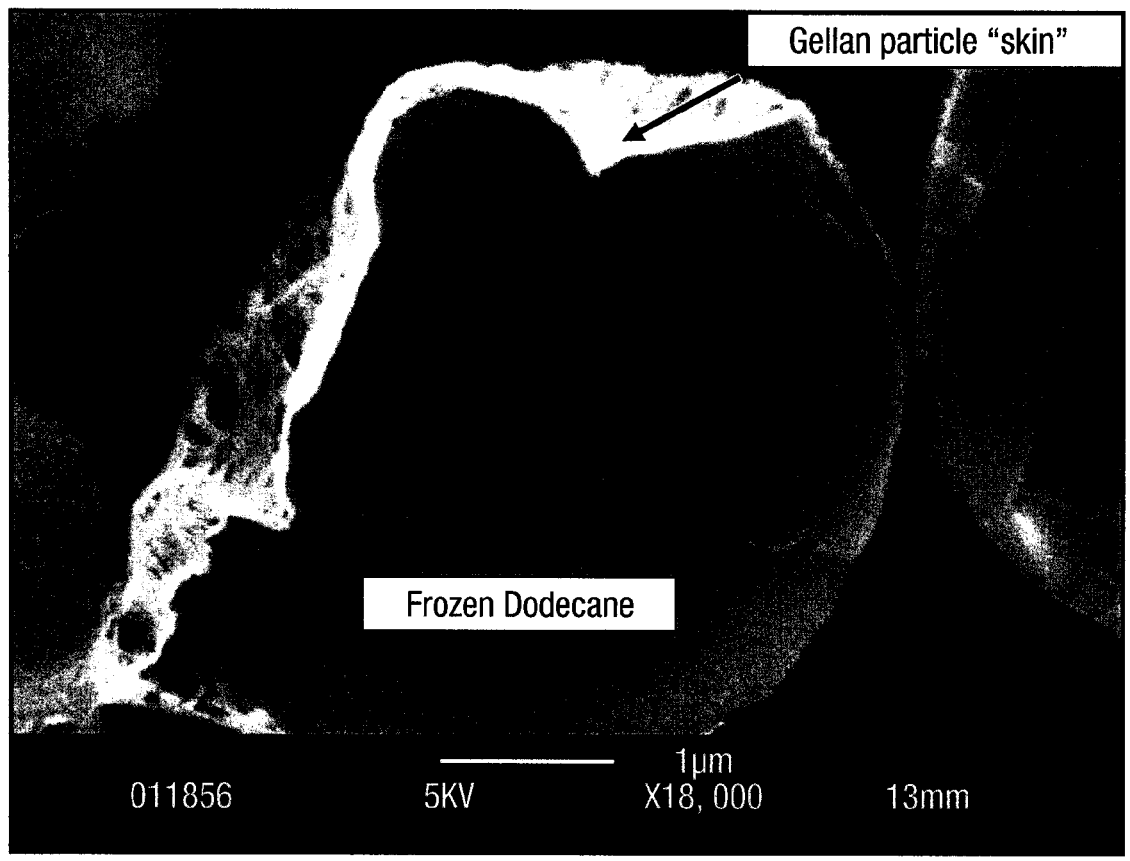
FIG. 14 a cryo-SEM image of a dodecane oil droplet stabilised by gellan gelled particles according to example 7.
Figure 15A:
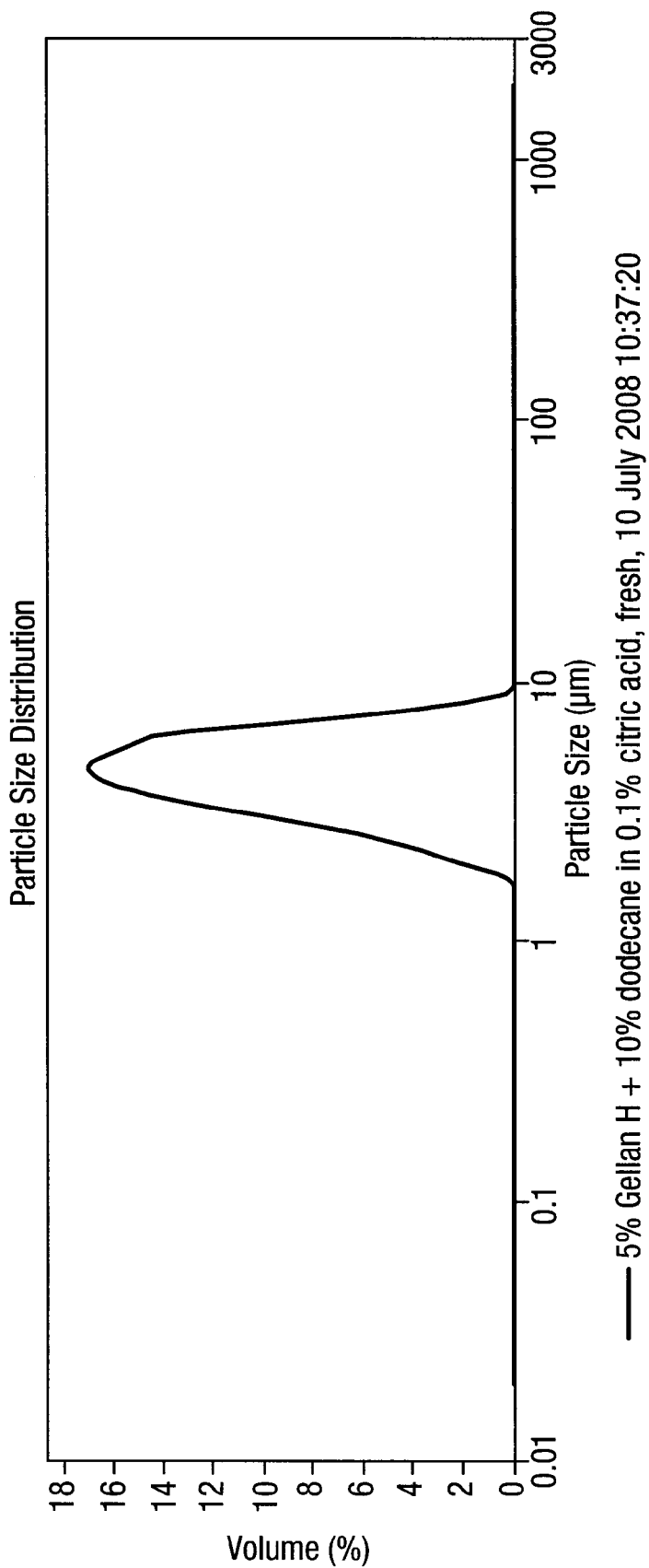
FIG. 15 the oil droplet size distribution of the dodecane-in-water-emulsion stabilised with gellan gelled particles emulsion of example 7 obtained by light scattering after storage at 4 degrees centigrade for 0 (FIG. 15a) and 42 (FIG. 15b) days respectively.
Figure 15B:
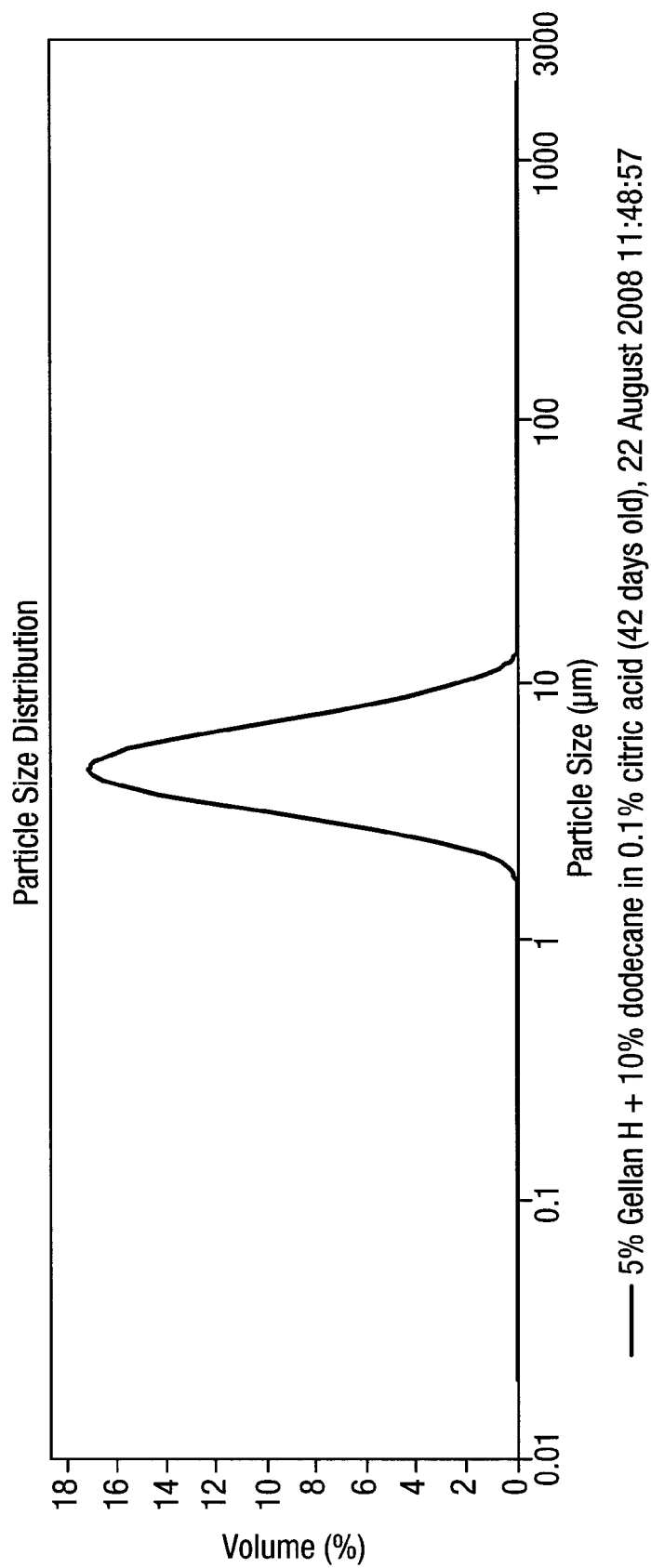

A 10% w/w dodecane-in-water emulsion was prepared with 5% w/w of the gellan gelled particles in a similar fashion to the method described in example 2. FIG. 14 shows a cryo-SEM image obtained using the method described in example 2 of a dodecane oil droplet stabilised by gellan gelled particles at pH 3.0 in 0.1 % citric acid. A layer or skin of gellan gelled particles appears to surround the dodecane droplet. FIGS. 15a and 15b shows the oil droplet size distribution of the emulsion obtained using the Malvern Mastersizer 2000 with the method outlined in example 1 after storage at 4

EXAMPLE 8

Preparation of a Dodecane-in-Water Emulsion Stabilised by Pectin Gelled Particles Prepared by Acid Hydrolysis 2% w/w pectin (Sigma Pectin, esterified potassium salt from citrus fruit Code P9311) was added to water at 100° C. and stirred for 1 hour to fully dissolve. The solution was then cooled to 70° C., the pH adjusted to 3.0 by the addition of citric acid and the resulting solution gently stirred for 2 hours. The pH was then adjusted to 1.0 using HCl aqueous solution and the mixture stirred for a further 15 minutes at 70° C. Finally the solution was combined with an equal volume of 1% w/w $CaCl_2$ aqueous solution to give a final concentration in water of 1% w/w pectin and 0.5% w/w $CaCl_2$. The solution was then cooled to chill temperature (4° C.) and particles allowed to form. The particles were washed thrice with 0.5% w/w $CaCl_2$ aqueous solution using the protocol described in example 1 with the final wash solution also containing 0.1% w/w citric acid and 0.1% w/w potassium sorbate as preservatives.

Figure 16:
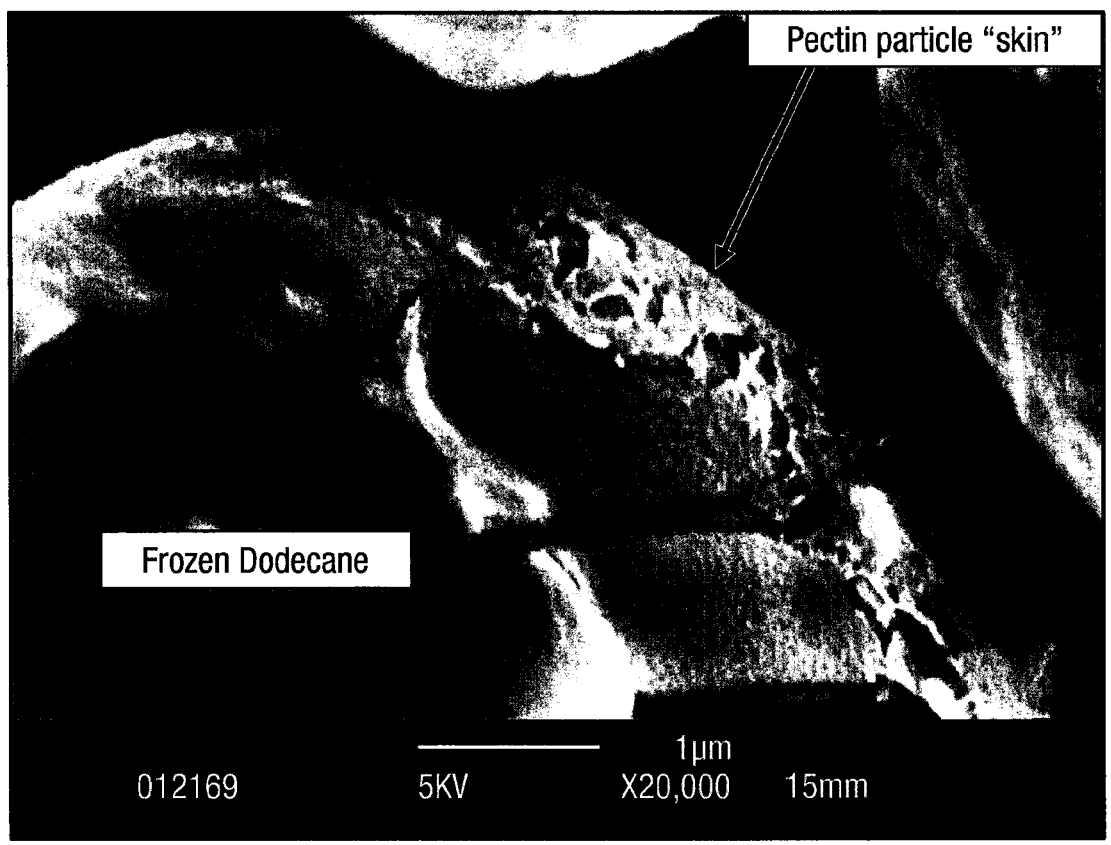
FIG. 16 a cryo-SEM image obtained using the method described in example 2 of a dodecane oil droplet stabilised by the pectin gelled particles of example 8.
Figure 17A:
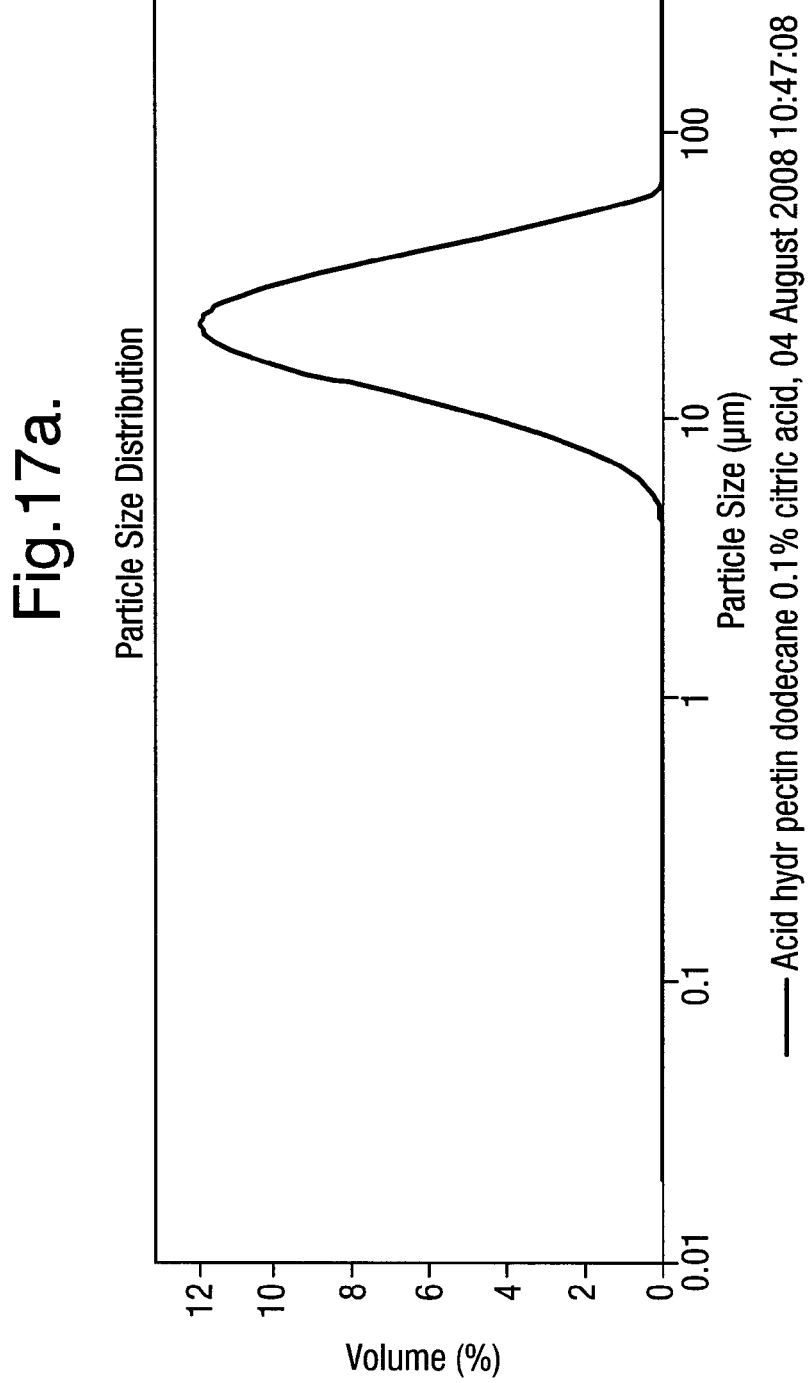
FIG. 17 the oil droplet size distribution of the dodecane-in-water-emulsion stabilised with pectin gelled particles emulsion of example 8 obtained by light scattering after storage at 4 degrees centigrade for 0 (FIG. 17a) and 10 (FIG. 17b) days respectively.
Figure 17B:
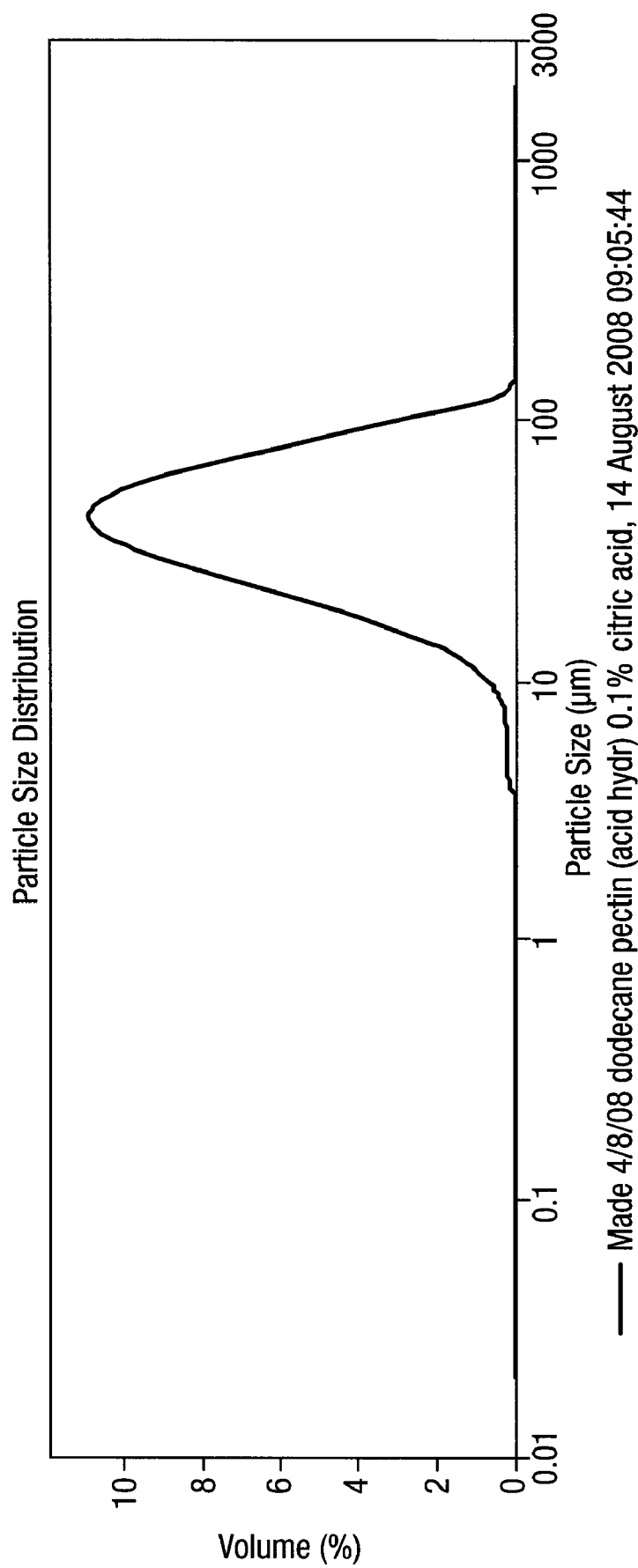

The particles were collected from the storage solution by centrifugation for 10 minutes at 3000 rpm on a MSE Centaur 2 centrifuge 3 grams of particles re-suspended in 97 grams of 0.1% w/w citric acid aqueous solution. 5 g of dodecane was then emulsified with 95 g of the 3% w/w suspension of particles and. using a Silverson L4R mixer set at high speed (speed setting 5) for 30 seconds. FIG. 16 shows a cryo-SEM image obtained using the method described in example 2 of a dodecane oil droplet stabilised by the pectin gelled particles. A layer or skin of pectin gelled particles appears to surround the dodecane droplet. FIGS. 17a and 17b shows the oil droplet size distribution of the emulsion obtained using the Malvern Mastersizer 2000 with the method outlined in example 1 after storage at 4 degrees centigrade for 0 (FIG. 17a) and 10 (FIG. 17b) days respectively indicating good emulsion stability.

EXAMPLE 9

Preparation of a Dodecane-in-Water Emulsion Stabilised by Pectin Gelled Particles Prepared by Alkaline Hydrolysis 2% w/w pectin (Sigma Pectin, esterified potassium salt from citrus fruit Code P9311) was added to water at 100° C. and stirred for 1 hour to fully dissolve. The solution was then cooled to 70° C., the pH adjusted to 12.0 by the addition of 1 N NaOH and the resulting solution gently stirred for 15 minutes. The solution was combined with an equal volume of 1% w/w $CaCl_2$ aqueous solution to give a final concentration in water of 1% w/w pectin and 0.5% w/w $CaCl_2$. The solution was then cooled to chill temperature (4° C.) and particles allowed to form. The particles were washed thrice with 0.5% w/w $CaCl_2$ aqueous solution using the protocol described in example 1 with the final wash solution also containing 0.1% w/w citric acid and 0.1% w/w potassium sorbate as preservatives.

Figure 18A:
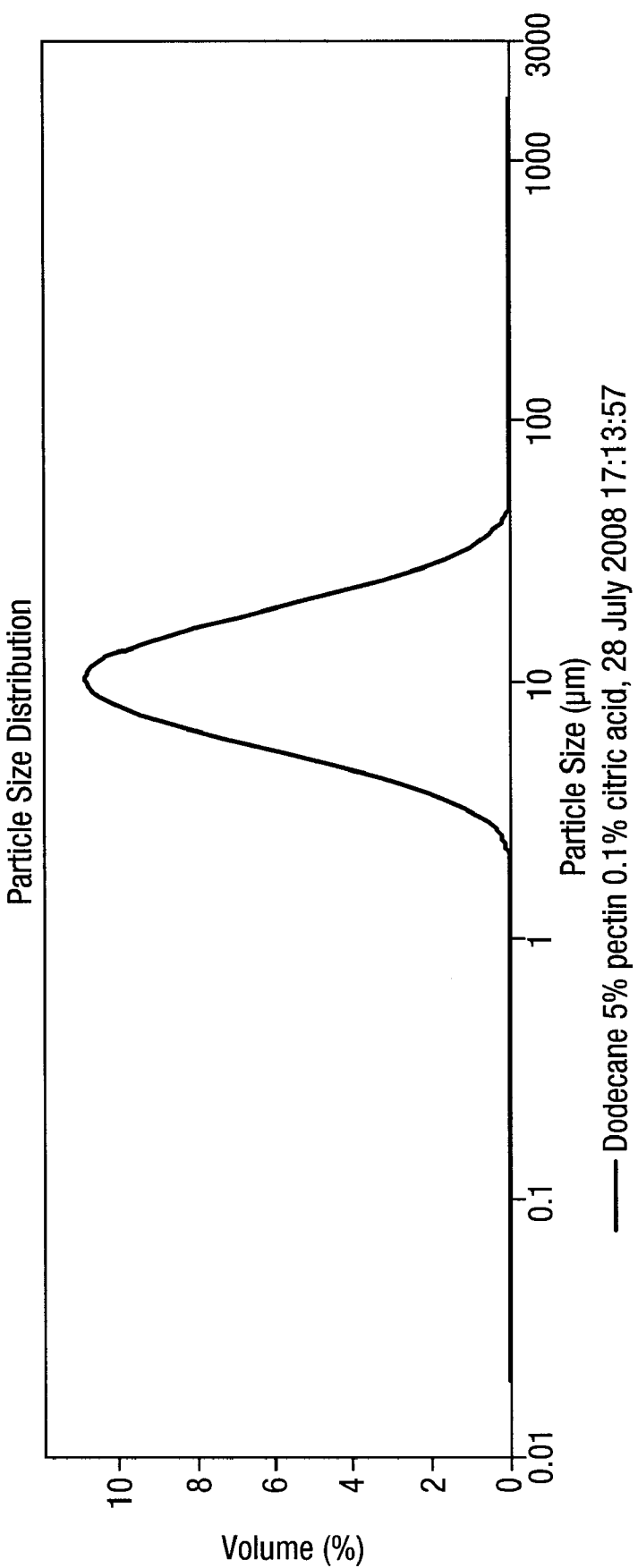
FIG. 18 the oil droplet size distribution of the dodecane-in-water-emulsion stabilised with pectin gelled particles emulsion of example 9 obtained by light scattering after storage at 4 degrees centigrade for 0 (FIG. 18a) and 17 (FIG. 18b) days respectively.
Figure 18B:
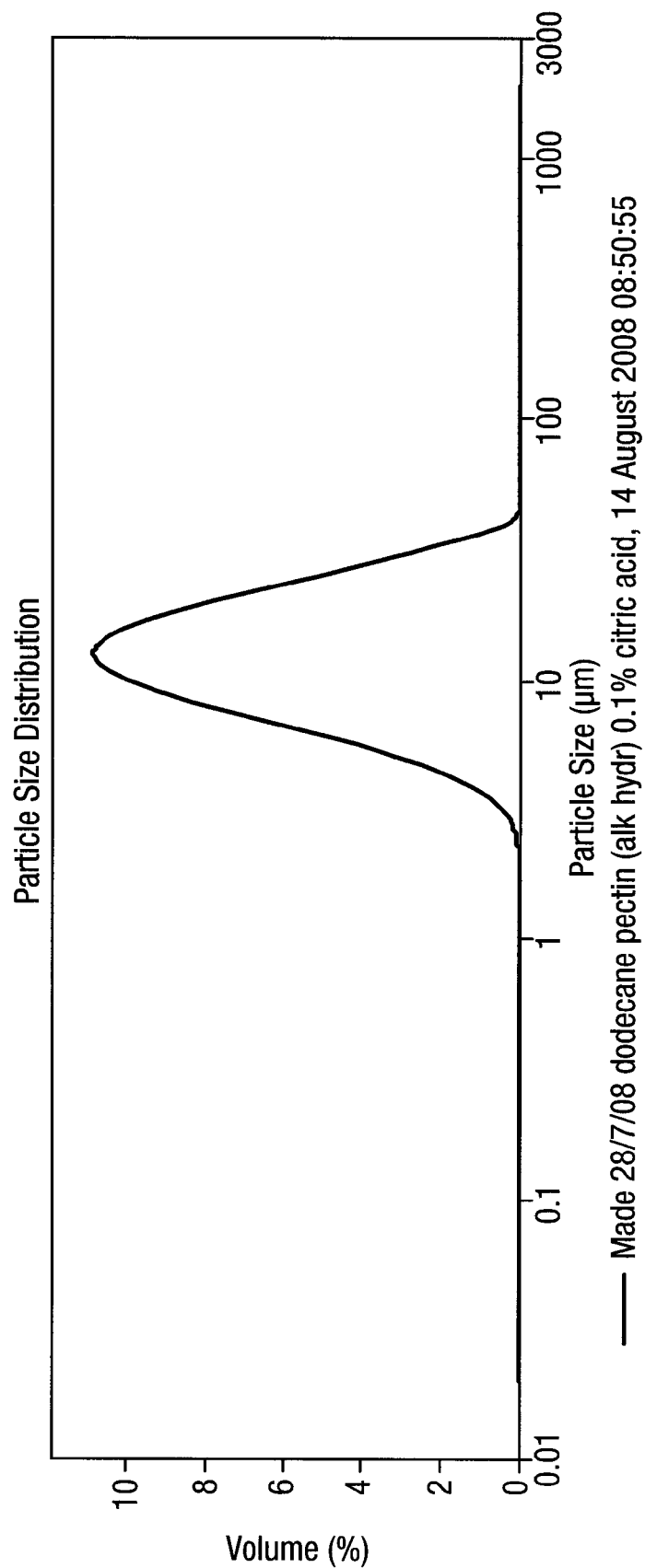

A dodecane-in-water emulsion stabilised by pectin gelled particles prepared by alkaline hydrolysis was prepared in a similar manner to as described in example 9. FIGS. 18a and 18b shows the oil droplet size distribution of the emulsion obtained using the Malvern Mastersizer 2000 with the method outlined in example 1 after storage at 4 degrees centigrade for 0 (FIG. 18a) and 17 (FIG. 18b) days respectively indicating good emulsion stability.

The invention claimed is:

1. An emulsion composition comprising as an emulsifier 0.5-25.0% by weight of the composition of gelled particles, wherein the gelled particles have a largest dimension of 5-500 nm, wherein the gelled particles (a) comprise at least one gellable hydrolyzed polysaccharide selected from the group consisting of agar, agarose, gellan and pectin, and (b) have an aspect ratio in the range of 1:1 to 10:1.

2. An emulsion composition according to claim 1, wherein the gelled particles are in the form of spheres, disks or rods.

3. An emulsion composition according to claim 1 comprising no emulsifier other than the described gelled particles.

4. An emulsion composition according to claim 1 selected from the group consisting of food products, home care products, personal care products and pharmaceutical products.

5. The emulsion composition according to claim 1, wherein the gelled particles have a water content of from 30-99.95% by weight, based on the total weight of the gelled particles.

6. The emulsion composition according to claim 1, wherein the gelled particles have a water content of from 90-99.95% by weight, based on the total weight of the gelled particles.

7. The emulsion composition according to claim 1 that is an oil-in-water emulsion.

8. The emulsion composition according to claim 1 wherein the gelled particles have a largest dimension of 10-200 nm.

9. The emulsion composition according to claim 1 having a dispersed phase of droplets having a largest dimension of up about 100 microns.

10. The emulsion composition according to claim 9 wherein the ratio of the largest dimension of the droplets which form the dispersed phase of the emulsion composition to the largest dimension of the gelled particles is in the range of 10:1 to 10000:1.

11. The emulsion composition according to claim 1 wherein the emulsion composition is in the form of a oil-in water emulsion, a water-in oil emulsion or a multiple emulsion, wherein the gelled particles stabilize the composition's oil-water interface(s).

12. The emulsion composition according to claim 11 wherein the composition is a multiple emulsion having a plurality of oil-water interfaces.

13. The emulsion composition according to claim 1 wherein the composition comprises from 0.5 to 10% by weight of the gelled particles.

* * * * *